US010036744B2

(12) United States Patent
Afzali-Ardakani et al.

(10) Patent No.: US 10,036,744 B2
(45) Date of Patent: Jul. 31, 2018

(54) BIFUNCTIONAL ACID MONOLAYERS FOR THE SELECTIVE PLACEMENT OF CARBON NANOTUBES

(71) Applicant: International Business Machines Corporation, Armonk, NY (US)

(72) Inventors: Ali Afzali-Ardakani, Ossining, NY (US); James B. Hannon, Lake Lincolndale, NY (US); George S. Tulevski, Croton-on-Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 82 days.

(21) Appl. No.: 14/974,562

(22) Filed: Dec. 18, 2015

(65) Prior Publication Data

US 2017/0176427 A1 Jun. 22, 2017

(51) Int. Cl.
*H01M 4/04* (2006.01)
*G01N 33/543* (2006.01)
*B82Y 40/00* (2011.01)

(52) U.S. Cl.
CPC ........ *G01N 33/54346* (2013.01); *B82Y 40/00* (2013.01)

(58) Field of Classification Search
CPC ............. G01N 33/54346; B82Y 40/00; H01M 4/0404; H01M 4/04
USPC ........................................................... 427/58
See application file for complete search history.

(56) References Cited

U.S. PATENT DOCUMENTS 7,504,132 B2 † 3/2009 Afzali-Ardakani
7,732,119 B2 7/2010 Afzali-Ardakani et al.
7,951,424 B2 5/2011 Afzali-Ardakani et al.
8,084,012 B2 12/2011 Afzali-Ardakani et al.
8,394,727 B1 3/2013 Afzali-Ardakani et al.
8,772,782 B2 7/2014 Cao et al.
9,177,688 B2 * 11/2015 Bol ..................... H01L 51/0048
9,273,004 B2 * 3/2016 Afzali-Ardakani .. C07D 213/76
2007/0236138 A1 * 10/2007 Hu ........................ B82Y 10/00 313/504
2013/0082233 A1 4/2013 Afzali-Ardakani et al.
2014/0361281 A1 * 12/2014 Carroll ................ H01L 51/0036 257/40
2014/0363638 A1 * 12/2014 Lobez Comeras .... C08G 75/00 428/201
2014/0363643 A1 * 12/2014 Afzali-Ardakani .... C08G 75/06 428/210
2017/0141319 A1 * 5/2017 Noh .................... H01L 51/0049

FOREIGN PATENT DOCUMENTS

WO WO 2008142375 A2 * 11/2008 ............. B82Y 30/00

OTHER PUBLICATIONS

Jonghoo Joo et al., "Dose-Controlled, Floating Evaporative Self-assembly and Alignment of Semiconducting Carbon Nanotubes from Organic Solvents", Langmuir 2014, 30, 3460-3466.*
Nish et al., "Highly selective dispersion of single-walled carbon nanotubes using aromatic polymers," Nature Nanotechnology, vol. 2, pp. 640-646 (Oct. 2007).
Park et al., "High-density integration of carbon nanotubes via chemical self-assembly," nature nanotechnology, pp. 1-5 (Oct. 2012).
C. Klinke et al., "Interaction of solid organic acids with carbon nanotube field effect transistors," Chemical Physics Letters, vol. 430, No. 1, Aug. 2006, pp. 75-79.
J.B. Hannon et al., "Selective placement of carbon nanotubes on metal-oxide surfaces," Langmuir, vol. 21, No. 19, Sep. 2005, pp. 8569-8571.

* cited by examiner
† cited by third party

*Primary Examiner* — Douglas J McGinty
(74) *Attorney, Agent, or Firm* — Vazken Alexanian; Michael J. Chang, LLC

(57) ABSTRACT

Techniques for selective placement of carbon nanotubes using bifunctional acid monolayers are provided. In one aspect, a method for selective placement of carbon nanotubes on a metal oxide surface includes the steps of: dispersing poly-fluorene polymer-wrapped carbon nanotubes in an organic solvent; creating a patterned monolayer of a bifunctional acid on the metal oxide surface, wherein the bifunctional acid comprises a first acid functional group for binding to the metal oxide surface, and a second acid functional group for binding to the poly-fluorene polymer-wrapped carbon nanotubes; and contacting the poly-fluorene polymer-wrapped carbon nanotubes dispersed in the organic solvent with the patterned monolayer of the bifunctional acid on the metal oxide surface to selectively place the carbon nanotubes on the metal oxide surface via the patterned monolayer of the bifunctional acid. A carbon nanotube-based device and method of formation thereof are also provided.

14 Claims, 4 Drawing Sheets

700

BIFUNCTIONAL ACID MONOLAYERS FOR THE SELECTIVE PLACEMENT OF CARBON NANOTUBES

FIELD OF THE INVENTION

The present invention relates to carbon nanotubes, and more particularly, to techniques for selective placement of carbon nanotubes using bifunctional acid monolayers.

BACKGROUND OF THE INVENTION

Carbon nanotubes may be used in a variety of different applications such as sensors, supercapacitors, electrodes, drug-delivery, and digital logic. However, many of these applications require that the carbon nanotubes be selectively placed onto specific areas of the device rather than producing a blanket film. The selective placement of carbon nanotubes can be challenging.

The low solubility of carbon nanotubes in most solvents provides one notable challenge. For instance, when the solvent is water, techniques have been proposed to wrap the carbon nanotubes in poly(thiophene)s which aids in dispersing the carbon nanotubes. The poly(thiophene)s have charged side chains which aid in the selective placement of the carbon nanotubes on a selectively charged surface. See, for example, U.S. Patent Application Publication Number 2014/0363643 by Afzali-Ardakani et al., entitled "Surface-Selective Carbon Nanotube Deposition Via Polymer-Mediated Assembly." These techniques are however limited to the specific type of solvent.

Techniques have been proposed for dispersing carbon nanotubes in solvents such as toluene by wrapping the carbon nanotubes in a polymer poly(9,9-dioctylfluorenyl-2,7-diyl). This permits effective dispersion of the carbon nanotubes in the solvent. See, for example, Nish et al., "Highly selective dispersion of single-walled carbon nanotubes using aromatic polymers," Nature Nanotechnology, vol. 2, pgs. 640-646 (October 2007) (hereinafter "Nish"). To date, however, no effective techniques exist for selective placement of carbon nanotubes from dispersions made in organic solvents such as toluene.

Therefore, improved carbon nanotube selective placement techniques would be desirable.

SUMMARY OF THE INVENTION

The present invention provides techniques for selective placement of carbon nanotubes using bifunctional acid monolayers. In one aspect of the invention, a method for selective placement of carbon nanotubes on a metal oxide surface is provided. The method includes the steps of: dispersing poly-fluorene polymer-wrapped carbon nanotubes in an organic solvent; creating a patterned monolayer of a bifunctional acid on the metal oxide surface, wherein the bifunctional acid comprises a first acid functional group for binding to the metal oxide surface, and a second acid functional group for binding to the poly-fluorene polymer-wrapped carbon nanotubes; and contacting the poly-fluorene polymer-wrapped carbon nanotubes dispersed in the organic solvent with the patterned monolayer of the bifunctional acid on the metal oxide surface to selectively place the carbon nanotubes on the metal oxide surface via the patterned monolayer of the bifunctional acid.

In another aspect of the invention, a carbon nanotube-based device is provided. The carbon nanotube-based device includes: a substrate comprising a metal oxide layer; a patterned monolayer of a bifunctional acid on the metal oxide layer, wherein the bifunctional acid comprises a first acid functional group for binding to the metal oxide surface, and a second acid functional group for binding to the poly-fluorene polymer-wrapped carbon nanotubes; and poly-fluorene polymer-wrapped carbon nanotubes selectively present only on surfaces of the metal oxide layer covered by the patterned monolayer of a bifunctional acid.

In yet another aspect of the invention, a method for forming a carbon nanotube-based device is provided. The method includes the steps of: dispersing poly-fluorene polymer-wrapped carbon nanotubes in an organic solvent; providing a substrate comprising a metal oxide layer; creating a patterned monolayer of a bifunctional acid on the metal oxide layer, wherein the bifunctional acid comprises a first acid functional group for binding to the metal oxide layer, and a second acid functional group for binding to the poly-fluorene polymer-wrapped carbon nanotubes; contacting the poly-fluorene polymer-wrapped carbon nanotubes dispersed in the organic solvent with the patterned monolayer of the bifunctional acid on the metal oxide layer to selectively place the carbon nanotubes on the metal oxide layer via the patterned monolayer of the bifunctional acid; and forming metal contacts to the poly-fluorene polymer-wrapped carbon nanotubes.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques for selective placement of polymer-wrapped carbon nanotubes dispersed in organic solvents, such as toluene or dichloromethane, on metal oxide surfaces, such as hafnium oxide ($HfO_2$) surfaces. As will be described in detail below, the present techniques provide chemistry (bifunctional acid monolayers) that is used to create 'acidic' patterns or regions on an otherwise 'basic' surface (e.g., metal oxide). The pattern can be created using microcontact printing. The polymer interacts strongly with the acidic regions, leading to selective placement of carbon nanotubes at these locations.

Figure 1:
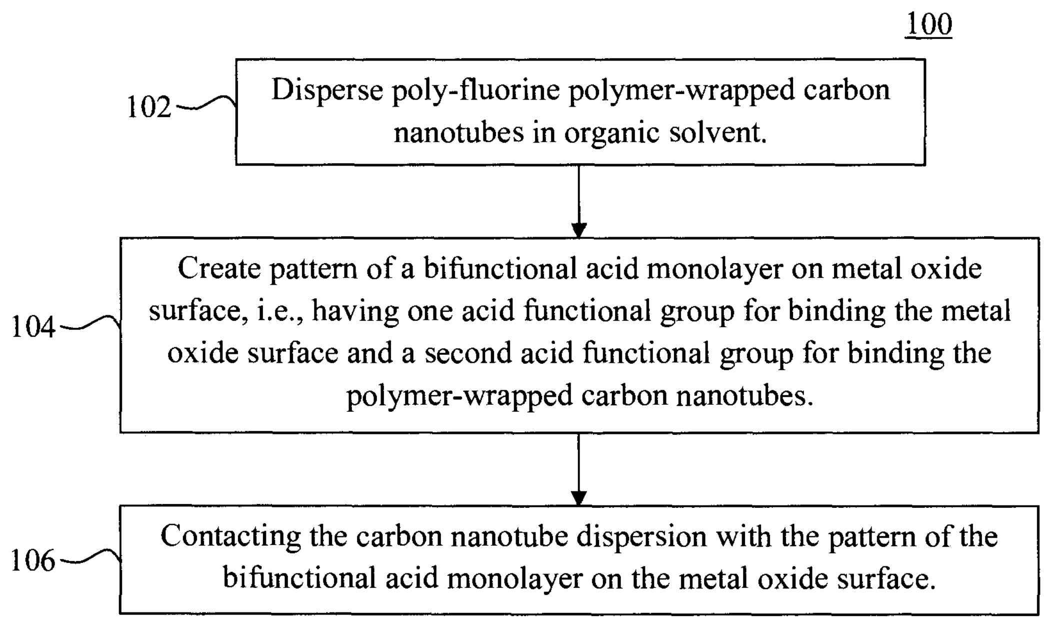
FIG. 1 is a diagram illustrating an exemplary methodology for selective placement of carbon nanotubes on a metal oxide surface according to an embodiment of the present invention.

FIG. 1 provides an exemplary methodology 100 for selective placement of carbon nanotubes on a metal oxide surface. In step 102 a dispersion of carbon nanotubes is prepared in an organic solvent. According to an exemplary embodiment, the organic solvent is selected from the group including toluene, dichloroethane, and combinations thereof. Dispersion of the carbon nanotubes in the solvent is achieved by wrapping the carbon nanotubes in an poly-fluorene aromatic polymer selected from the group including, poly[9,9-dioctylfluorenyl-2,7-diyl], poly[9,9-dihexyl-fluorenyl-2,7-diyl], poly[(9,9-dioctylfluorenyl-2,7-diyl)-co-(1,4-phenylene)], poly[(9,9-dioctylfluorenyl-2,7-diyl)-alt-co-(1,4-benzo-2,1',3-thiadiazole)], poly[(9,9-dioctylfluorenyl-2,7-diyl)-alt-co-(2,2'-bipyridine-5,5'-diyl)] and combinations thereof. See, for example, Nish, the contents of which are incorporated by reference as if fully set forth herein. According to an exemplary embodiment, the carbon nanotube dispersion is created by contacting single-walled carbon nanotubes with the aromatic polymer and the solvent. Carbon nanotubes are commercially available from, e.g., Sigma-Aldrich, St. Louis, Mo.

The bipyridine moiety of the above-described poly-fluorene aromatic polymer interacts strongly with acidic regions. Advantageously, this property is leveraged herein to allow for selective placement of the polymer-wrapped carbon nanotubes on the surface of the metal oxide layer by creating a patterned bifunctional acid monolayer on the metal oxide layer. By "bifunctional" it is meant that the patterned acid monolayer contains two acid functional groups, one that binds the monolayer to the metal oxide surface, and another that binds the (poly-fluorene) polymer-wrapped carbon nanotubes. By "monolayer" it is meant that the bifunctional acid forms a layer on the metal oxide layer that is on the order of one atom thick. By employing a monolayer, it will ensure that the acid functional groups are properly oriented vis-à-vis the metal oxide layer and the polymer-wrapped carbon nanotubes.

Further, as will be described in detail below, a single microcontact printing step can be used to produce the patterned bifunctional acid layer as a monolayer on the metal oxide layer, which greatly simplifies the present process. For instance, by comparison, conventional carbon nanotube self-assembly techniques involve (e.g., via lithography and etching) a silicon dioxide ($SiO_2$) pattern on the metal oxide surface. See, for example, Park et al., "High-density integration of carbon nanotubes via chemical self-assembly," nature nanotechnology, pgs. 1-5 (October 2012), the contents of which are incorporated by reference as if fully set forth herein.

According to an exemplary embodiment, the first acid functional group (to bind the monolayer to the metal oxide surface) is either hydroxamic acid or phosphonic acid, and the second acid (to bind to the polymer-wrapped carbon nanotubes dispersed in the organic solvent) is carboxylic acid, phosphoric acid, or sulfonic acid. By way of example only, the bifunctional acid may be synthesized as follows:

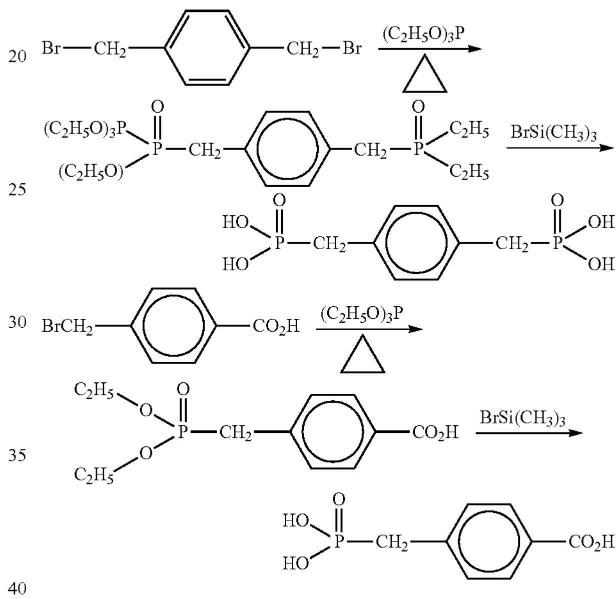

Thus, in step 104, a pattern of the bifunctional acid monolayer is created on the surface of the metal oxide layer. As provided above, the bifunctional acid monolayer can be created on the surface of the metal oxide layer using microcontact printing techniques. In general, microcontact printing involves using standard lithography and etching techniques to create a template from which a stamp is made. The stamp may be formed from an elastomer, such as a silicon elastomer. The material to be transferred to a substrate is then placed on the stamp, and the stamp is brought in physical contact with the substrate to 'print' the material on the substrate. The template/stamp contains the pattern the material will have on the substrate. In the present techniques, the template/stamp will have the final desired pattern of the carbon nanotubes on the metal oxide layer. Namely, the pattern on the stamp will be used to place the pattern of the bifunctional acid monolayer on the metal oxide surface. It is through this bifunctional acid monolayer that the (poly-fluorene) polymer-wrapped carbon nanotubes self-assemble on the metal oxide surface.

In step 106, the carbon nanotube dispersion is contacted with the pattern of the bifunctional acid monolayer on the surface of the metal oxide layer. By way of example only, the carbon nanotube dispersion can be sprayed, cast, etc. onto the surface of the metal oxide layer, or the metal oxide layer with bifunctional acid pattern can be soaked in the carbon nanotube dispersion. As a result of the interaction (i.e., acid/base) between the (second) acid functional groups in the bifunctional acid monolayer and the bipyridine moiety of the polymer-wrapped carbon nanotubes, the carbon nanotubes will assemble on the metal oxide surface where the bifunctional acid monolayer pattern exists. Due to the weak interaction between the polymer-wrapped carbon nanotubes and exposed areas of the metal oxide surface, few if any carbon nanotubes will be placed outside of the pattern.

Figure 2:
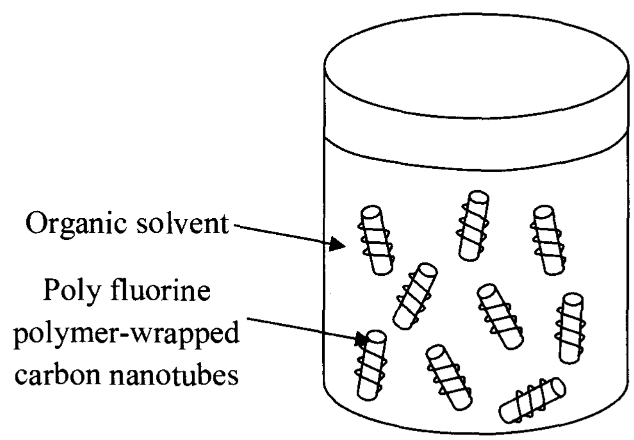
FIG. 2 is a schematic diagram illustrating a dispersion of poly fluorene polymer-wrapped carbon nanotubes having been prepared in an organic solvent according to an embodiment of the present invention.

Given the above overview of the present techniques, the steps of methodology 100 are now further illustrated by way of reference to FIGS. 2-6. As shown in FIG. 2, in accordance with step 102 of methodology 100, a dispersion of poly fluorene polymer-wrapped carbon nanotubes is prepared in an organic solvent (e.g., toluene and/or dichloroethane). Techniques for carbon nanotube dispersion in an organic solvent via a poly fluorene polymer are described, for example, in Nish.

Figure 3:
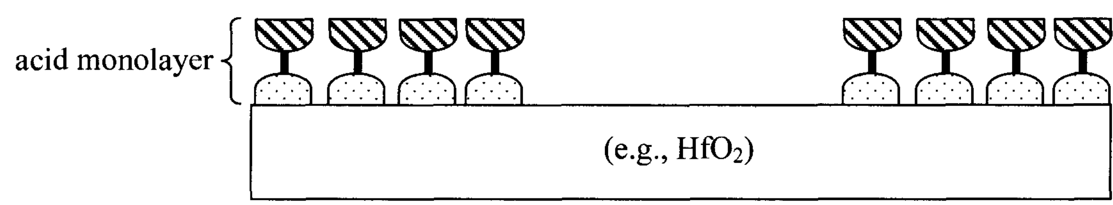
FIG. 3 is a cross-sectional diagram illustrating a monolayer pattern of a bifunctional acid having been formed on a metal oxide surface according to an embodiment of the present invention.

Next, as shown in FIG. 3, in accordance with step 104 of methodology 100, a monolayer (i.e., one-atom thick) pattern of a bifunctional acid is formed on the metal oxide (e.g., hafnium oxide ($HfO_2$)) surface. As FIG. 3 illustrates, the bifunctional acid monolayer contains a first acid functional group (e.g., hydroxamic acid or phosphonic acid) selective for binding the metal oxide, and a second acid functional group (e.g., carboxylic acid, phosphoric acid, or sulfonic acid) for binding the polymer-wrapped carbon nanotubes.

Figure 4:
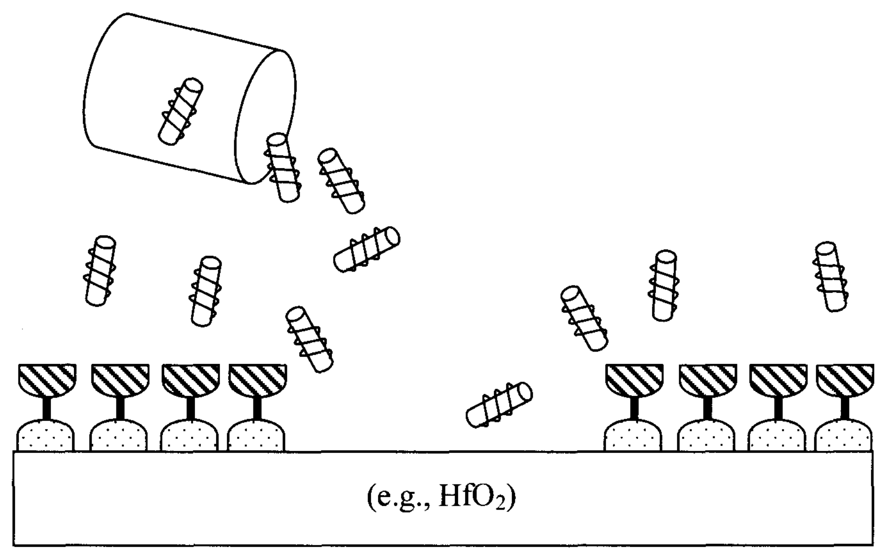
FIG. 4 is a cross-sectional diagram illustrating the polymer-wrapped carbon nanotube dispersion being deposited onto the pattern of the bifunctional acid monolayer on the metal oxide surface according to an embodiment of the present invention.
Figure 5:
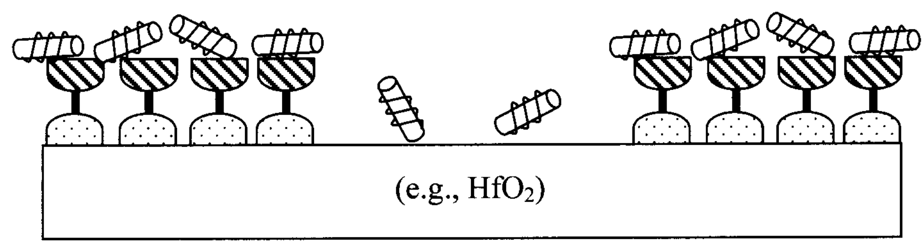
FIG. 5 is a cross-sectional diagram illustrating the polymer-wrapped carbon nanotubes having self-assembled on the metal oxide surface based on the pattern of the bifunctional acid monolayer according to an embodiment of the present invention.

As shown in FIG. 4, in accordance with step 106 of methodology 100, the polymer-wrapped carbon nanotube dispersion can then be deposited (e.g., by spraying, casting, soaking, etc.) onto the pattern of the bifunctional acid monolayer on the metal oxide surface. As shown in FIG. 5, the polymer-wrapped carbon nanotubes will self-assemble on the metal oxide surface based on the pattern of the bifunctional acid monolayer (due to the acid/base interaction of the poly-fluorene polymer with the functional groups on the acid monolayer.

Figure 6:
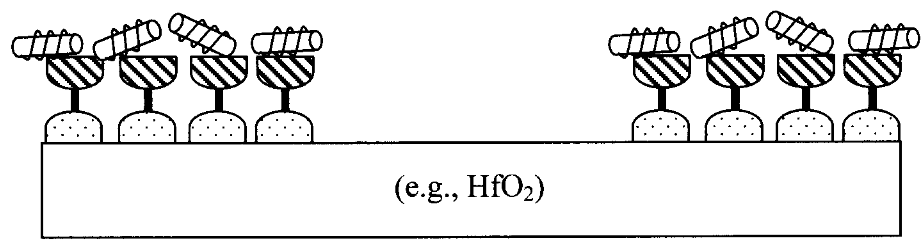
FIG. 6 is a cross-sectional diagram illustrating weakly adhering carbon nanotubes having been removed from the bare metal oxide surfaces according to an embodiment of the present invention.

A few of the carbon nanotubes might settle on bare surfaces of the metal oxide (i.e., surfaces of the metal oxide not covered by the pattern of the bifunctional acid monolayer) during this process. See FIG. 5. However, as shown in FIG. 6, a process such as sonication can serve to remove the weakly adhering carbon nanotubes from the bare metal oxide surfaces. Sonication will not disrupt the carbon nanotubes adhered to the pattern.

Figure 7:
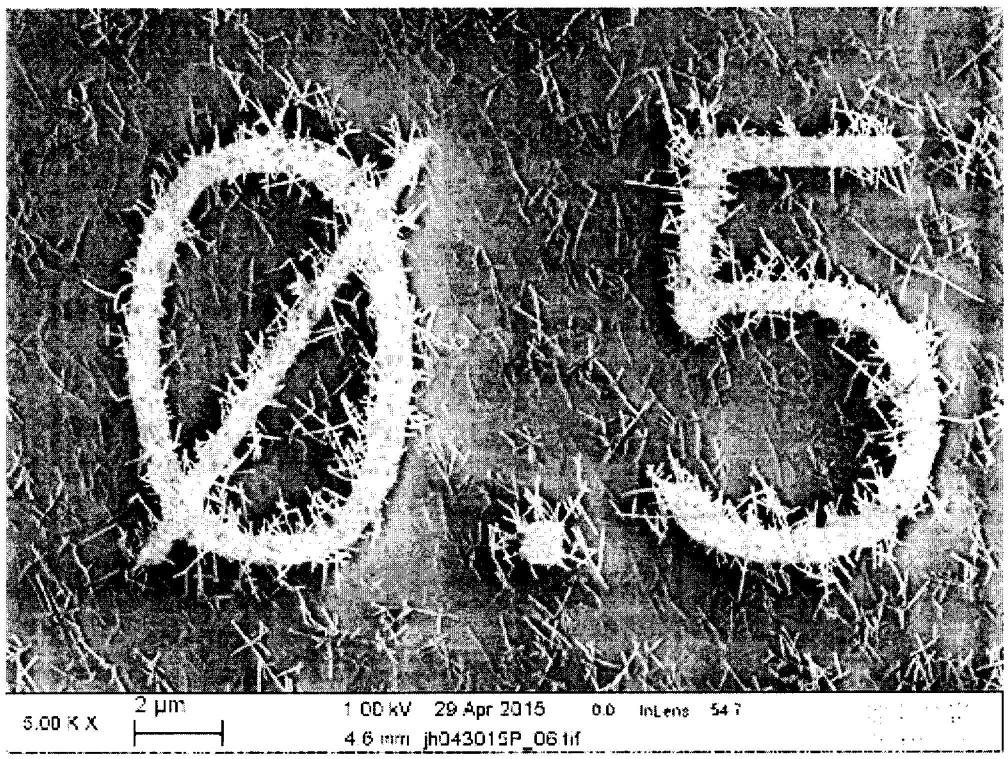
FIG. 7 is an image of a sample prepared using the present techniques according to an embodiment of the present invention.

For illustrative purposes only, FIG. 7 is an image 700 of a sample prepared using the present techniques. Specifically, image 700 is of a surface after exposure to (poly-fluorene) polymer-wrapped carbon nanotubes dispersed in toluene. The dark areas in the image are untreated $HfO_2$. The bright areas are 'acidic' $SiO_2$ regions. The density of carbon nanotubes on the acidic regions is far higher than that seen on the 'basic' $HfO_2$ regions.

Figure 8:
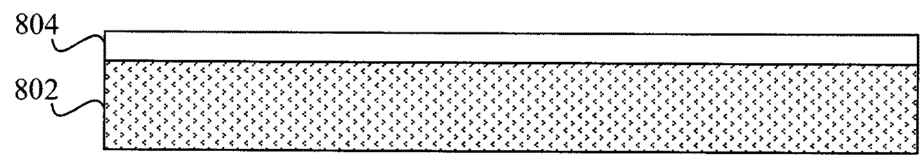
FIG. 8 is an cross-sectional diagram illustrating a substrate having a semiconductor wafer covered with a metal oxide dielectric layer according to an embodiment of the present invention.

A non-limiting, illustrative example implementing the present techniques in the fabrication of a carbon nanotube-based device is now described by way of reference to FIG. 8-11. As shown in FIG. 8, a substrate is provided. According to an exemplary embodiment, the substrate includes a semiconductor wafer 802 (such as a silicon (Si) wafer) covered with a dielectric layer 804. According to an exemplary embodiment, the dielectric layer includes a metal oxide such as $HfO_2$, and is the metal oxide surface on which the present techniques are used to self-assemble the carbon nanotubes. In some applications, the semiconductor wafer 802 might be doped, e.g., so as to serve as a back gate of the device. In such a configuration, the metal oxide 802 serves as a gate dielectric.

Figure 9:
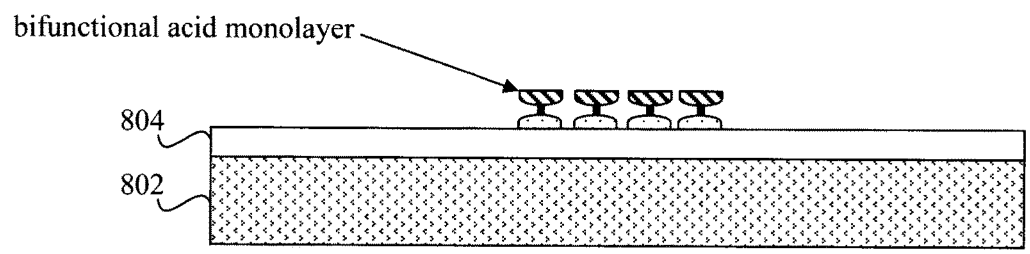
FIG. 9 is a cross-sectional diagram illustrating a pattern of the present bifunctional acid monolayer having been formed on the metal oxide layer according to an embodiment of the present invention.

As shown in FIG. 9, a pattern of the above-described bifunctional acid monolayer is formed on the metal oxide surface. As described above, the bifunctional acid monolayer contains one acid functional group (e.g., hydroxamic acid or phosphonic acid) selective for binding the metal oxide, and a second acid functional group (e.g., carboxylic acid, phosphoric acid, or sulfonic acid) for binding (poly fluorene) polymer-wrapped carbon nanotubes. It is noted that the structures and features depicted in the figures are not drawn to scale.

As provided above, microcontact printing techniques may be employed to form the patterned bifunctional acid monolayer on the metal oxide surface. In that case one might simply use the above-described stamping techniques to place the bifunctional acid monolayer at the exact desired location on the metal oxide layer.

Figure 10:
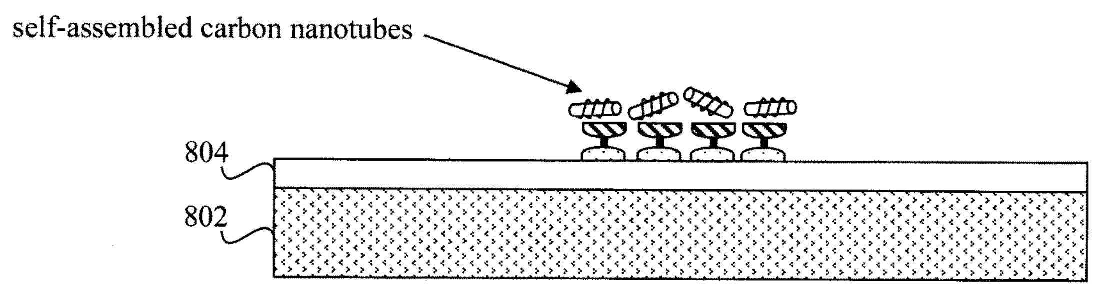
FIG. 10 is a cross-sectional diagram illustrating carbon nanotubes having been placed in a select location of the substrate on the metal oxide layer according to an embodiment of the present invention.

The above-described process may then be employed to deposit the (poly fluorene) polymer-wrapped carbon nanotube dispersion onto the pattern of the bifunctional acid monolayer on the metal oxide surface. Excess carbon nanotubes (such as those weakly adhering to bare metal oxide) can be easily (and selectively) removed using sonication. The result, as shown in FIG. 10, is the placement of the carbon nanotubes in a select location of the substrate on the metal oxide layer.

Contacts 1102 can then be formed to the carbon nanotubes. See FIG. 11. According to an exemplary embodiment, the contacts 1102 are metal contacts (e.g., gold (Au), titanium (Ti), etc.). Metal contacts 1102 can be formed using evaporation, sputtering, and/or conventional lift-off techniques.

In its simplest form, the device produced is a carbon nanotube-based transistor. In general, a transistor includes a source and a drain interconnected by a channel (formed by the carbon nanotubes in this case). A gate (often separated from the channel by a dielectric) serves to regulate the flow of electrons in the channel. In this exemplary implementation, the semiconductor substrate can be conductive (e.g., through doping—see above) so as to serve as a back gate electrode of the device, which is separated from the carbon nanotube channel by the (metal oxide) dielectric layer 804.

Figure 11:
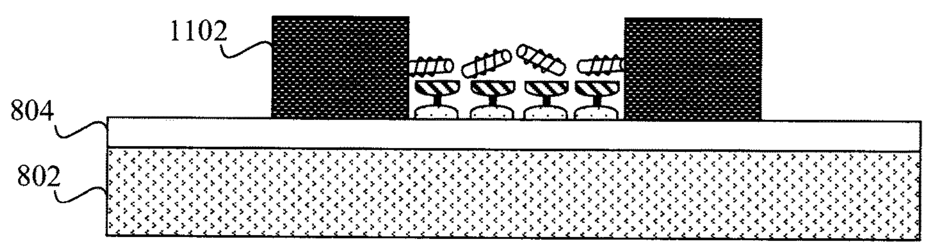
FIG. 11 is a cross-sectional diagram illustrating metal contacts having been formed to the carbon nanotubes according to an embodiment of the present invention.

This device configuration shown in FIG. 11 has a variety of different applications. For instance, this device can serve as the platform for building carbon nanotube-based sensors. Carbon nanotube-based sensors have been demonstrated in the art for detecting a variety of different target compounds, from biological specimens to gas and chemical sensing. As known in the art, the basic principle behind carbon nanotube-based sensors is that the surfaces of the carbon nanotubes can be functionalized with species (chemical compounds, DNA, antibodies, etc.) selective for binding a particular target compound. Upon binding, the target species changes the properties of the carbon nanotubes, and thus the switching properties of the device. For instance, the resistance of the carbon nanotubes (between the electrodes 1102) can change when a target species is bond to the carbon nanotubes.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for selective placement of carbon nanotubes on a metal oxide surface, the method comprising the steps of:

dispersing poly-fluorene polymer-wrapped carbon nanotubes in an organic solvent, wherein the organic solvent is selected from the group consisting of: toluene, dichloroethane, and combinations thereof;

creating a patterned monolayer of a bifunctional acid on the metal oxide surface, wherein the bifunctional acid comprises a first acid functional group for binding to the metal oxide surface, and a second acid functional group for binding to the poly-fluorene polymer-wrapped carbon nanotubes; and contacting the poly-fluorene polymer-wrapped carbon nanotubes dispersed in the organic solvent with the patterned monolayer of the bifunctional acid on the metal oxide surface to selectively place the carbon nanotubes on the metal oxide surface via the patterned monolayer of the bifunctional acid.

2. The method of claim 1, wherein the metal oxide surface comprises hafnium oxide.

3. The method of claim 1, wherein the poly-fluorene polymer is selected from the group consisting of: poly[9,9-dioctylfluorenyl-2,7-diyl], poly[9,9-dihexylfluorenyl-2,7-diyl], poly[(9,9-dioctylfluorenyl-2,7-diyl)-co-(1,4-phenylene)], poly[(9,9-dioctylfluorenyl-2,7-diyl)-alt-co-(1,4-benzo-2,1',3-thiadiazole)], poly[(9,9-dioctylfluorenyl-2,7-diyl)-alt-co-(2,2'-bipyridine-5,5'-diyl)] and combinations thereof.

4. The method of claim 1, further comprising the step of:

contacting the carbon nanotubes, the poly-fluorene polymer, and the organic solvent to form the poly-fluorene polymer-wrapped carbon nanotubes dispersed in the organic solvent.

5. The method of claim 1, wherein the first acid functional group is hydroxamic acid or phosphonic acid.

6. The method of claim 1, wherein the second acid functional group is carboxylic acid, phosphoric acid, or sulfonic acid.

7. The method of claim 1, wherein the patterned monolayer of a bifunctional acid is created on the metal oxide surface using microcontact printing.

8. The method of claim 1, further comprising the step of:

removing the carbon nanotubes from bare portions of the metal oxide surface.

9. The method of claim 8, wherein the carbon nanotubes are removed from the bare portion of the metal oxide surface using sonication.

10. A method for forming a carbon nanotube-based device, the method comprising the steps of:

dispersing poly-fluorene polymer-wrapped carbon nanotubes in an organic solvent, wherein the organic solvent is selected from the group consisting of: toluene, dichloroethane, and combinations thereof;

providing a substrate comprising a metal oxide layer;

creating a patterned monolayer of a bifunctional acid on the metal oxide layer, wherein the bifunctional acid comprises a first acid functional group for binding to the metal oxide layer, and a second acid functional group for binding to the poly-fluorene polymer-wrapped carbon nanotubes;

contacting the poly-fluorene polymer-wrapped carbon nanotubes dispersed in the organic solvent with the patterned monolayer of the bifunctional acid on the metal oxide layer to selectively place the carbon nanotubes on the metal oxide layer via the patterned monolayer of the bifunctional acid; and forming metal contacts to the poly-fluorene polymer-wrapped carbon nanotubes.

11. The method of claim 10, wherein the poly-fluorene polymer is selected from the group consisting of: poly[9,9-dioctylfluorenyl-2,7-diyl], poly[9,9-dihexylfluorenyl-2,7-diyl], poly[(9,9-dioctylfluorenyl-2,7-diyl)-co-(1,4-phenylene)], poly[(9,9-dioctylfluorenyl-2,7-diyl)-alt-co-(1,4-benzo-2,1',3-thiadiazole)], poly[(9,9-dioctylfluorenyl-2,7-diyl)-alt-co-(2,2'-bipyridine-5,5'-diyl)] and combinations thereof.

12. The method of claim 10, wherein the first acid functional group is hydroxamic acid or phosphonic acid.

13. The method of claim 10, wherein the second acid functional group is carboxylic acid, phosphoric acid, or sulfonic acid.

14. The method of claim 1, wherein the poly-fluorene polymer is poly[(9,9-dioctylfluorenyl-2,7-diyl)-alt-co-(2,2'-bipyridine-5,5'-diyl)].

* * * * *